United States Patent [19]

Hoffman

[11] Patent Number: 5,087,883
[45] Date of Patent: Feb. 11, 1992

[54] DIFFERENTIAL CONDUCTIVITY METER FOR FLUIDS AND PRODUCTS CONTAINING SUCH METERS

[75] Inventor: Ronald J. Hoffman, Solon, Ohio

[73] Assignee: Mr. Coffee, inc., Bedford Heights, Ohio

[21] Appl. No.: 579,941

[22] Filed: Sep. 10, 1990

[51] Int. Cl.$^5$ .............................................. G01N 27/02
[52] U.S. Cl. ..................................... 324/443; 324/446; 324/450
[58] Field of Search ............... 324/439, 443, 444, 446, 324/450, 405; 422/82.02, 99, 101, 102; 436/177, 806

[56] References Cited

U.S. PATENT DOCUMENTS

| | | | |
|---|---|---|---|
| 3,781,659 | 12/1973 | Ur | 324/450 |
| 3,938,034 | 2/1976 | Japenga | 324/405 |
| 4,331,923 | 5/1982 | Akers, Jr. | 324/446 X |
| 4,455,530 | 6/1984 | Lee et al. | 324/446 |
| 4,814,281 | 3/1989 | Byers | 422/82.02 X |

*Primary Examiner*—Jack B. Harvey
*Attorney, Agent, or Firm*—D. Peter Hochberg; Mark Kusner; Louis J. Weisz

[57] ABSTRACT

A device for detecting relative differences in conductivity between filtered and unfiltered states of fluid comprises a differential comparator for measuring the voltage difference of its input ports, a differential bridge connected to the input sorts of the differential comparator for measuring the conductivity of the fluid, the differential bridge having electrodes for contacting the fluid in each of its filtered and unfiltered states and bridge adjustment circuitry for compensating for voltage offsets of the comparator and the bridge, and an indicator connected to the output of the comparator for generating an output indicative of the differential conductivity of the fluid in its filtered and unfiltered states.

14 Claims, 3 Drawing Sheets

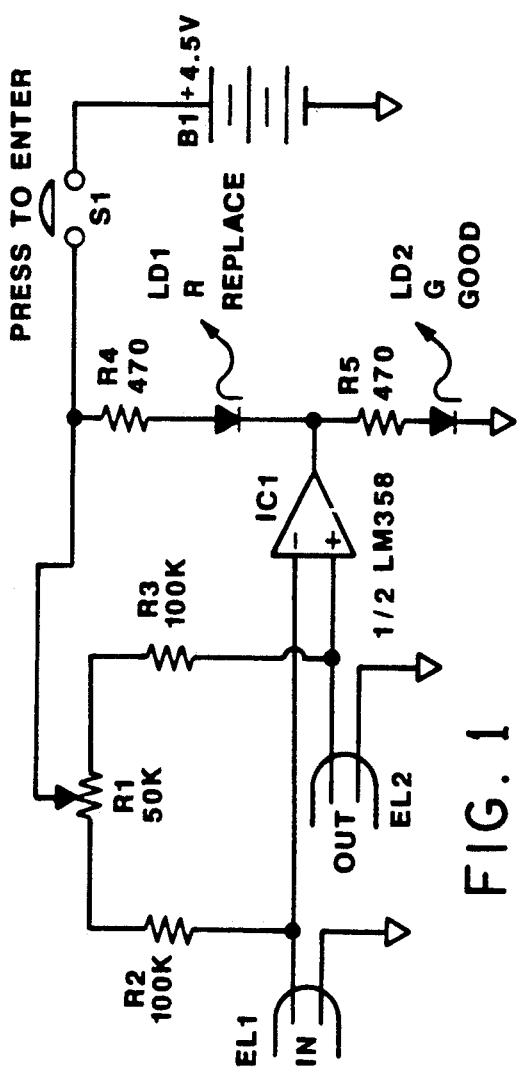
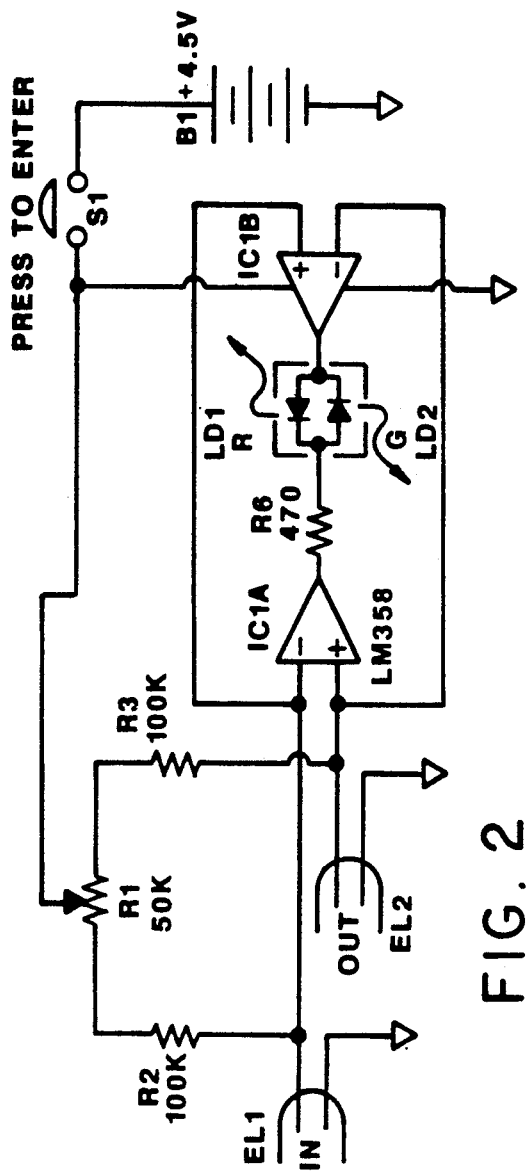

DIFFERENTIAL CONDUCTIVITY METER FOR FLUIDS AND PRODUCTS CONTAINING SUCH METERS

TECHNICAL FIELD

This invention relates to a device for determining the point at which a liquid filter, especially a water filter, has reached the end of its useful life or otherwise is not functioning properly. More particularly, this invention relates to the measurement of electrical conductivity as a means for determining the presence or absence of undesirable impurities in liquids processed through a filter capable of removing the same. Specifically, this invention relates to means for simultaneously determining the differential electrical conductivity of filtered water or other fluid relative to the same unfiltered water, and the use of such difference to ascertain the effectiveness of the filtration and, therefore, the condition of the filter.

BACKGROUND OF THE INVENTION

Water filters which remove unwanted minerals, chemicals, bacteria, sediments, etc. have been in wide use for many years. They use a combination of activated charcoal, silver and various types of resin beads as filter means to remove the undesirable elements from the incoming water. Some filters only remove elements related to hardness, like $Ca++$, $Mg++$, $Cd++$, $Ba++$, $Hg++$, $Na+$, $Cu+$, $K+$, (positive ions), while others remove $Cl-$, $Br-$, $I-$, (negative ions). Other filters remove both kinds of ions from water and are referred to as de-ionizers. The activated charcoal removes unwanted organic molecules and elements which cause bad taste. Small amounts of silver kills bacteria and water borne viruses. The water conductivity is reduced when the ions and unwanted chemicals are removed from solution after passing through the filtering means. Depending upon the concentration of minerals, chemicals and organisms present in the unfiltered water, the filter life can vary greatly. A filter could last for a month or a year depending on the condition of the water which is being filtered. It would be desirable to find an inexpensive electronic means to measure the filter to determine if it is saturated or used up. After conducting many tests, it was determined that conductivity can be used as a measure of filter effectiveness. When the conductivity of the filtered water is nearly equal to the input water, the resin is saturated and the filter should be replaced. Since water conductivity may vary greatly depending upon local water treatment, geographic location, water temperature, chemical softening and the like, not only will the length of filter life change, but the filter efficiency will produce only a relative drop in conductivity of the filtered water. To cancel out relative filter efficiency, wide ranging input water conductivities, different input water temperatures and other variables, a differential conductivity measurement provides the correct results using a minimum of parts and reduces production costs allowing wide use in several consumer product applications.

BRIEF DESCRIPTION OF THE INVENTION

In view of the preceding, therefore, it is the first aspect of this invention to provide apparatus to determine the state of efficiency of a filter for purifying fluids.

It is a second aspect of this invention to provide apparatus to measure the relative purity of different samples of fluids electronically.

It is a further aspect of this invention to provide apparatus to determine the relative electrical conductivity of liquids on each side of an in-line filter.

It is also an aspect of this invention to determine the relative electrical conductivity of liquids employing a direct current power source without measurement-impairing plating of the electrodes.

It is an additional aspect of this invention to provide an inexpensive device to determine the relative conductivity of water, both before and after it has been filtered.

Another aspect of this invention is to provide a portable, hand-held device for determining the relative electrical conductivity of fluid samples.

Still a further aspect of this invention is to provide a two-chambered vessel having a filter disposed therein in which a liquid placed in one chamber passes through the filter as it proceeds to a second chamber, the vessel being provided with means to determine the relative electrical conductivity of the liquid in the chambers.

The preceding and other aspects of this invention are provided in preferred embodiments thereof by a differential conductivity meter for detecting the difference in conductivity between a sample of unfiltered fluid, and fluid after it has been filtered. The meter comprises a differential comparator means having an input means and an output means, for measuring the voltage differential of the input means, and a differential bridge means for measuring conductivity of the fluid. The bridge means includes electrode means for contacting the fluid, and bridge adjustment means operatively connected to the electrode means and to the comparator means, to compensate for voltage offsets of the differential bridge means and the differential comparator means. Indicator means is operatively connected to the differential comparator means for generating an output indicative of the differential conductivity of the fluid.

The invention can include or be useable with a fluid vessel having at least two compartments with at least one area where fluid can flow from one compartment to the other, filtering means for filtering fluid passing from one compartment to the other to alter the anionic conductivity of the fluid, and further including the differential conductivity meter described above.

The foregoing differential conductivity meter can comprise in preferred embodiments a circuit board conductivity meter having a circuit board, electrode means disposed on at least two areas of the circuit board, and fluid compartment means operatively connected to the electrode means.

A preferred embodiment of the invention comprises a portable conductivity meter comprising circuit board means, electrode means insertable into compartments containing fluid whose conductivity is to be measured, and other parts of the differential conductivity meter means described earlier.

Another preferred embodiment of the invention comprises in-line conductivity meter comprising circuit board means, electrode means insertable into fluid lines at the inlet and outlet of the in-line filtering means through which the fluid passes, and the differential conductivity meter means discussed above.

BRIEF DESCRIPTION OF THE DRAWINGS

The invention will be better understood when reference is had to the following figures, in which like-numbers refer to like-parts, and in which:

FIG. 1 is a circuit diagram of a differential electrical conductivity indicating device of the invention;

FIG. 2 is a circuit diagram of another embodiment of the device of FIG. 1;

DETAILED DESCRIPTION OF THE INVENTION

Figure 3:
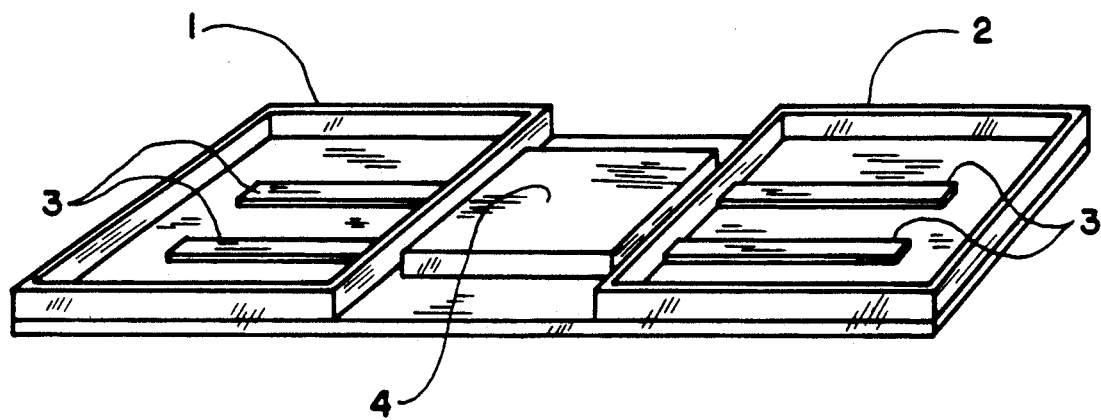
FIG. 3 is an isometric view of a differential electrical conductivity indicating device of the invention.

FIG. 1 is a circuit diagram of a differential electrical conductivity indicating device of the invention, two pairs of electrodes EL1 and EL2, respectively, which form a differential resistance bridge with a variable resistor trim pot R1 and resistors R2 and R3. The trim pot R1, the resistor R2, and electrode EL1 form one leg of the resistance bridge. Trim pot R1, resistor R3 and electrode EL2 form the second leg of the second leg of the bridge. By suitable adjustment to the trim pot R1, the resistance bridge can be adjusted to compensate for resistance tolerance of resistors R1 and R3. The trim pot further serves to adjust for input offsets found in comparator IC1 and any physical differences between the two sets of electrodes EL1 and EL2, i.e., spacing of the electrodes, their effective areas, sizes and the like.

While the resistors R2 and R3 could be omitted without destroying the essential balance of the bridge, any necessary trim is supplied by adjustment of the trim pot R1. The resistors are also used to decrease the adjustment sensitivity of R1, and are preferred. Electrodes EL1 and EL2 are placed in distilled water and trim pot R1 is adjusted until the red light emitting diode (LED), identified as LD1, is just turned "ON". Following this adjustment, whenever the electrode EL2 is placed in water that is less conductive than the water around electrode EL1, indicating a functioning filter, the voltage to the positive input of the comparator IC1 increases and goes "positive" with respect to the negative input of comparator IC1 which is connected to electrode EL1. The bridge is then unbalanced and the electrode node voltages are offset. This causes the output voltage of the comparator IC1 to go "high", which in turn causes the green LED, identified as LD2, to light.

The consequence of the circuit action described is that when the filter supplying the water in which the EL2 electrode is immersed, the filtered water, containing conductive ions, will have the same conductivity as the unfiltered water into which electrode EL1 has been placed. When the filter no longer removes conductive ions from the water, electrodes EL1 and EL2 have the same conductivity. Due to the adjusted offset of trim-pot R1, the electrode node voltages make the positive input of comparator IC1 negative with respect to the negative input of IC1. The comparator IC1 output is then be negative which causes the red LED, LD1 to light. This indicates that the filter needs to be replaced.

The resistance values indicated for R1, 50,000 ohms, and R2 and R3, 100,000 ohms, as well as the resistance values of resistors R4 and R5 associated with the LEDs, 470 ohms, will depend upon the electrical characteristics of the circuit, including its various components, and may be varied in ways well known in the art. The comparator illustrated is a dual op-amp comparator, only one-half of which is operative in the circuit of FIG. 1. The comparator illustrated is an LM 358 manufactured by the National Semi-Conductor Company; however, other equivalent comparators manufactured by other companies are also suitable.

The circuit is shown connected to a 4.5 volt battery, B1, supplying current through a switch S1 of the momentary type that requires the application of continuing pressure to maintain their activation. Other types of switches, however, may also be employed for the purpose.

Because this is a differential measurement, the effect of temperature is canceled out by the bridge since it affects both electrodes equally. The effect of water conductivity is also canceled out by the differential bridge. The only parameter which is measured is the change in conductivity of the water after it has passed through the filter means compared with the conductivity of the original input water. The differential measurement eliminates all of the calibration and accuracy which would be required if an absolute conductivity measurement were being performed.

To minimize the effects of plating on the electrode sensors EL1 and EL2, the circuit is turned on by a momentary switch activated by the user only when the filter needs to be tested. The measurement current is preferably kept below 50 micro-amperes, voltage is preferably kept at 4.5 volts, and nickel plated electrodes are used which are less prone to plating effects or corrosion in water. The current drain on the batteries is about 10 milli-amps only when the test is being made. If each test required 3 seconds (0.05 minutes), and the batteries were rated for 100 milli-amp-hours, the number of tests is equal to the battery amp-hour rating divided by the current times the length of the test. In this example, 0.1 amp-hr × 60 min/hr (0.01 amp × 0.05 min), or 6 amp-min/0.0005 amp-min, which equals 12,000 filter tests on a single set of batteries.

FIG. 2 is a circuit diagram of another embodiment of the device of FIG. 1, which is very similar to the circuit of FIG. 1 except, however, that comparator IC1 has been replaced by a first comparator IC1A and a second comparator IC1B. Please refer to the schematic diagram in FIG. 2. By using the second comparator IC1B, and connecting it just the opposite of comparator IC1A, the red LED, LD1, and the green LED, LD2, can be connected in parallel but in opposite directions and placed in series with a single resistor to reduce cost and parts count by one resistor. Both embodiments may be used as a matter of choice, but the second method may have some display flicker due to the unequal voltage threshold of the two comparators.

FIG. 3 is an isometric view of a differential electrical conductivity indicating device of the invention. As shown, the device comprises an unfiltered liquid receptacle 1, and a receptacle for holding filtered liquids 2. Both receptacles are attached to a circuit board. Sets of nickel plated electrodes 3 are located in each of the receptacles and attached to the circuit board. The electrodes are connected to a differential conductivity detection circuit 4. The user fills the unfiltered water receptacle 1 with unfiltered water and fills the filtered water receptacle 2 with filtered water. When the button of circuit 4 is pressed, the activation of the red indicator LED of circuit 4 indicates that the filter was not working, while activation of the green indicator LED of circuit 4 indicates that the filter was working.

Figure 4:
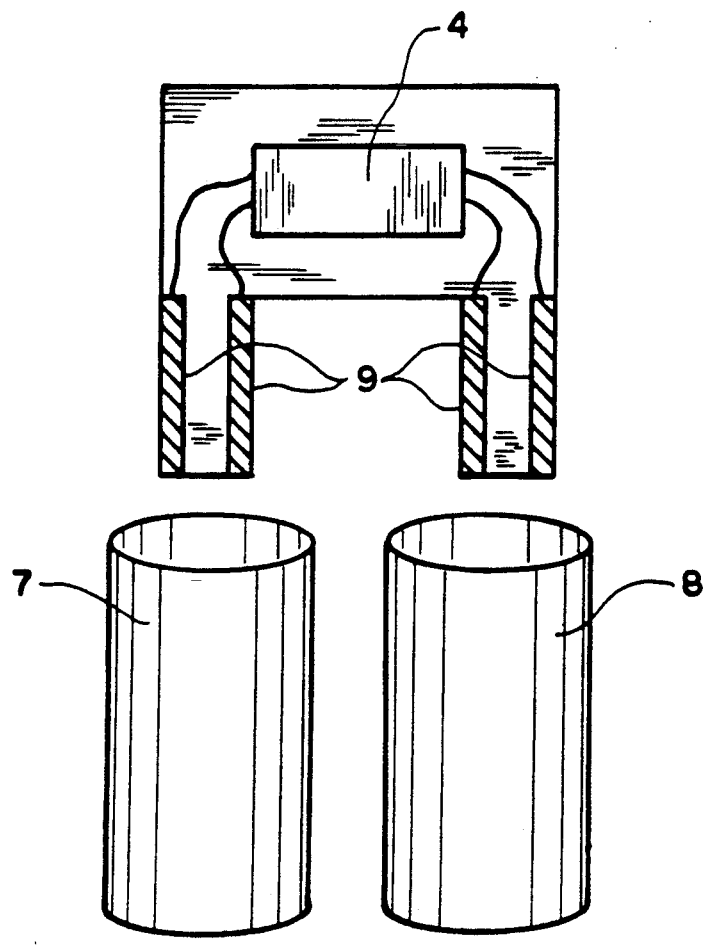
FIG. 4 is an illustration of a hand-held differential electrical conductivity indicating device of the invention.

FIG. 4 illustrates of a hand-held differential electrical conductivity unit of the invention showing an unfiltered liquid receptacle 7 and a filtered liquid receptacle 8. The hand-held unit has two electrode assemblies 9 protruding from a circuit board on which they are attached. The hand-held unit also has a differential conductivity detection circuit 4. The user merely inserts the two electrode probes into the receptacles containing filtered and unfiltered water and presses the test switch button of circuit 4. Activation of the red LED of circuit 4 indicates a malfunctioning filter, while lighting of the green LED of circuit 4 shows that the filters operating properly. The illustrations of FIGS. 3 and 4 show general purpose instruments which can be used to test any filter by comparing samples of the water both before and after filtration in separate containers.

Figure 5:
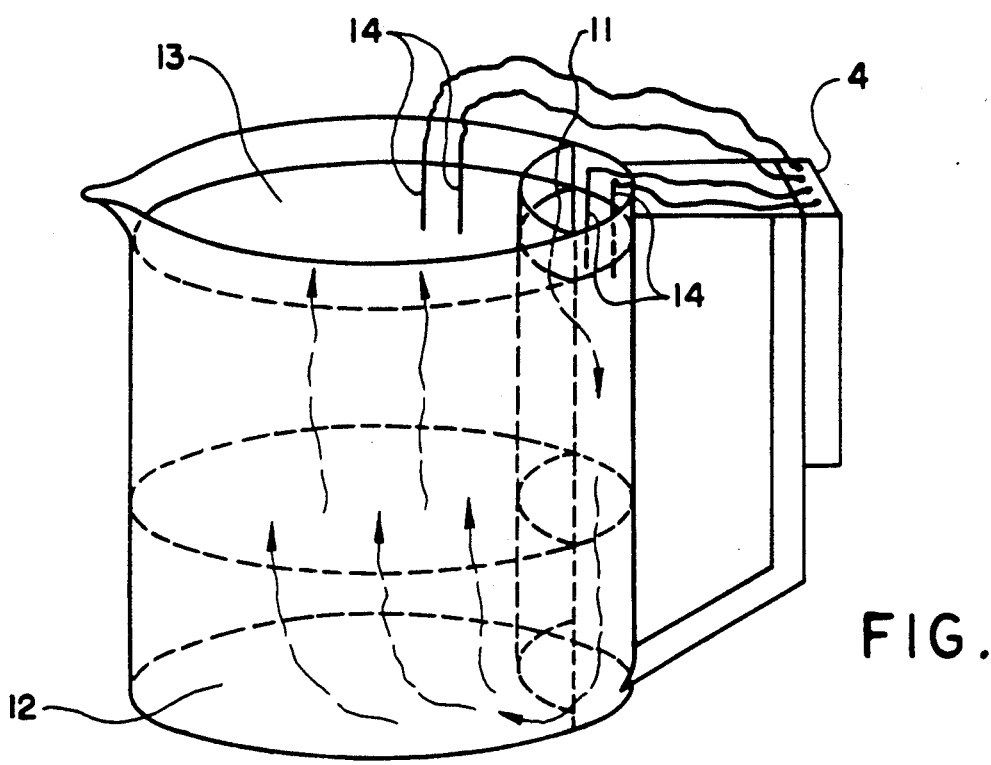
FIG. 5 is an isometric view of a two-chambered liquid filtering vessel that includes a differential conductivity indicating means according to the invention.
Figure 6:
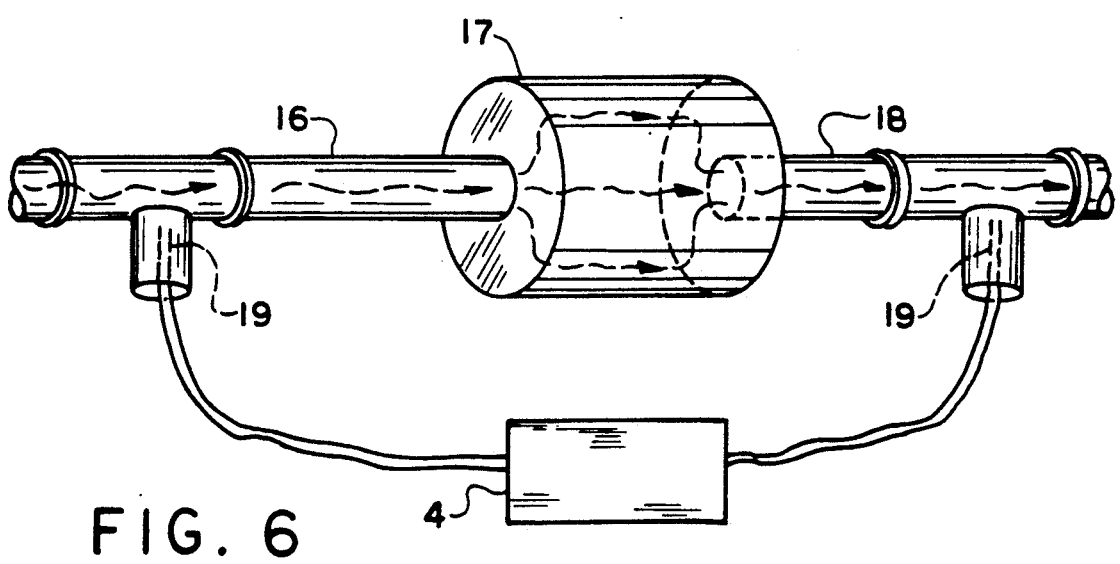
FIG. 6 is an isometric view of an in-line filter associated with the differential conductivity indicating means according to the invention.

FIGS. 5 and 6 illustrate embodiments where the circuit is applied as part of an appliance or in-line filtering device. In FIG. 5, the device is shown as a pitcher which has two compartments 11 and 13 and a partition which extends down near the bottom of the vessel. A filter 12 is secured at the bottom of chamber 13, of the filtered water compartment. One set of electrodes 14 is located in each of the compartments. The electrode probes are connected to a differential conductivity detection circuit 4. A user pours water into the unfiltered compartment 11 either directly or by means of the funnel/lid. The water passes through the filter 12 and rises in the filtered water compartment 13. When the pitcher is full, the water level in the filtered and unfiltered compartments will be equal. The pair of electrode probes in each water compartment measures the filtered and unfiltered conductivity as described in connection with FIG. 3, that is, to determine whether the filter is working correctly. While not shown, the operating switch and indicating LEDs are similar to those previously described.

In FIG. 6, the conductivity electrodes are placed in fittings which can be inserted in-line with an under-the-sink in-line filter cartridge. The unit can be tested periodically after running the water to determine if the filter cartridge is still filtering properly. Line 16 provides unfiltered water to a filter 17, the water thereafter leaving through line 18. Electrodes 19 are provided in both the incoming and outgoing lines, being attached to a differential conductivity detection circuit 4. As previously described, the temporary closing of the switch of circuit 4 lights either the red LED or the green LED of circuit 4, confirming whether or not the filter has been exhausted, depending upon which light is activated.

While the invention has been described in connection with the filtration of water, the invention is equally useful with other polar liquids capable of conducting electric current.

While in accordance with the patent statutes, a preferred embodiment and best mode has been presented, the scope of the invention is not limited thereto, but rather is measured by the scope of the attached claims.

What is claimed is:

1. A differential conductivity meter for detecting the difference in conductivity between a sample of unfiltered fluid and a sample of filtered fluid, said meter comprising:

momentary switch means for applying power from a battery to said meter for a brief period of time to extend battery life, for actuating said meter to detect the difference in conductivity:

differential comparator means having an input means and an output means, for measuring the voltage difference of the input means;

direct current differential bridge means for measuring the differential conductivity of said unfiltered fluid and said filtered fluid, said bridge means including:

electrode means connected to the input means of said differential comparator for contacting said filtered fluid and said unfiltered fluid; and bridge adjustment means operatively connected to said electrode means and said comparator means, to compensate for voltage offsets of said differential bridge means and said differential comparator means;

wherein said differential bridge means detects only the differential conductivity of said unfiltered fluid and said filtered fluid and eliminates the effects of the fluid temperature and the amounts of absolute conductivity of the fluid; and wherein the short actuation of said momentary switch means to detect the difference in fluid conductivity substantially minimizes electrode plating; and indicator means operatively connected to the output means of said differential comparator means for generating an output indicative of the differential conductivity of said fluid samples.

2. The invention according to claim 1 wherein said bridge adjustment means is comprised of adjustable resistor means.

3. The invention according to claim 1 for use with a two-chambered vessel having filtering means wherein the two chambers are operatively connected at the bottom so that unfiltered fluid introduced into a first of the chambers passes through the filtering means at the bottom of the vessel and rises in the other chamber, and wherein said electrode means are disposed in the fluid in each of the two chambers, to measure the difference in electrical conductivity between the filtered and unfiltered fluid.

4. The invention according to claim 1, and further including:

circuit board means;

said electrode means being disposed on two areas of the circuit board means; and, fluid container means operatively connected to said electrode means;

wherein a sample of filtered fluid can be placed in one of said container means and a sample of unfiltered fluid can be placed in the other of said container means, to detect the difference in conductivity between the filtered and unfiltered fluid.

5. The invention according to claim 1 for use with an in-line filter wherein said electrode means are placed in filter lines entering and leaving said filter to detect the difference in conductivity before and after the fluid passes through said filter.

6. The invention according to claim 1 for use as a hand-held instrument, said electrode means being insertable into separate containers containing filtered and unfiltered fluid, respectively, to detect the difference in conductivity between the filtered and unfiltered fluid.

7. A vessel for containing fluids comprising:
two compartments having at least one area where fluid can flow from one compartment to the other;
filtering means for filtering fluid passing from one compartment containing unfiltered fluid to the other to alter the ionic conductivity of the fluid to produce a filtered fluid; and
differential conductivity meter means for detecting the difference in conductivity between fluid in said compartments, said meter means comprising:
momentary switch means for applying power from a battery to said meter means for a brief period of time to extend battery life and for actuating said meter means to detect the difference in conductivity:
differential comparator means having an input means and output means, for measuring the voltage difference of the input means; and
direct current differential bridge means for measuring the differential conductivity of said unfiltered fluid and said filtered fluid, said bridge means including:
electrode means for contacting the fluid in each of said compartments, and
bridge adjustment means operatively connected to said electrode means and to said differential comparator means to compensate for voltage offsets of said differential bridge means and said differential comparator means for generating an output indicative of the differential conductivity of the fluid in said compartments;
wherein said differential bridge means detects only the differential conductivity of said unfiltered fluid and said filtered fluid and eliminates the effects of the fluid temperature and the amounts of absolute conductivity of the fluid; and
wherein the short actuation of said momentary switch means to detect the difference in fluid conductivity substantially minimizes electrode plating; and
indicator means operatively connected to said differential comparator means for generating an output indicative of the differential conductivity of said fluids.

8. The invention according to claim 7 wherein said bridge adjustment means is comprised of adjustable resistor means.

9. A circuit board conductivity meter for detecting the difference between unfiltered fluid and filtered fluid, said meter comprising:
a circuit board,
fluid compartment means; and
differential conductivity meter means for detecting the difference in conductivity between unfiltered fluid and filtered fluid in said compartment means, said meter means comprising:
momentary switch means for applying power from a battery to said meter means for a brief period of time to extend battery life and for actuating said meter means to detect the difference in conductivity;
differential comparator means having an input means and output means for measuring the voltage difference of the input means; and
direct current differential bridge means for measuring the differential conductivity of said unfiltered fluid and said filtered fluid, said bridge means including:
electrode means disposed on at least two areas of said circuit board for contacting the fluid in each of said compartment means; and
bridge adjustment means operatively connected to said electrode means and to said comparator means to compensate for voltage offsets of said differential bridge means and said comparator means, said comparator means generating an output indicative of the differential conductivity of the fluid in said comparator means; and
wherein said differential bridge means detects only the differential conductivity of said unfiltered fluid and said filtered fluid and eliminates the effects of the fluid temperature and the amounts of absolute conductivity of the fluid; and
wherein the short actuation of said momentary switch means to detect the difference in fluid conductivity substantially minimizes electrode plating; and
indicator means operatively connected to the output means of said differential comparator means for generating an output indicative of the differential conductivity of said fluid.

10. The invention according to claim 9 wherein said bridge adjustment means is comprised of adjustable resistor means.

11. A portable device for measuring the conductivity differential in fluid in its filtered and unfiltered states, said device comprising:
circuit board means;
differential conductivity meter means for detecting the difference in conductivity between a fluid in its filtered and unfiltered states, said meter comprising:
momentary switch means for applying power from a battery to said meter means for a brief period of time to extend battery life and for actuating said meter means to detect the difference in conductivity;
differential comparator means having an input means and output means for measuring the voltage difference of the input means;
direct current differential bridge means for measuring the differential conductivity of said unfiltered fluid and said filtered fluid, said bridge means comprising:
electrode means attached to said circuit board means for contacting the unfiltered fluid and the filtered fluid; and
bridge adjustment means operatively connected to said electrode means and to said comparator means to compensate for voltage offsets of said differential bridge means and said differential comparator means, said differential comparator means generating an output indicative of the differential conductivity of the fluid; and
wherein said differential bridge means detects only the differential conductivity of said unfiltered fluid and said filtered fluid and eliminates the effects of the fluid temperature and the amounts of absolute conductivity of the fluid; and
wherein the short actuation of said momentary switch means to detect the difference in fluid conductivity substantially minimizes electrode plating; and indicator means operatively connected to said differential comparator means for generating an output indicative of the differential conductivity of the fluid.

12. The invention according to claim 11 wherein said bridge adjustment means is comprised of adjustable resistor means.

13. An in-line conductivity device for use with an in-line filtering means having an inlet and an outlet for fluid lines, said device comprising:

circuit board means;

differential conductivity meter means for detecting the difference in conductivity between unfiltered fluid and filtered fluid in said fluid lines, said meter means comprising:

momentary switch means for applying power from a battery to said meter means for a brief period of time to extend battery life and for actuating said meter means to detect the difference in conductivity;

differential comparator means having an input means and output means for measuring the voltage difference of the input means; and direct current differential bridge means for measuring the differential conductivity of said unfiltered fluid and said filtered fluid, said bridge means including:

electrode means on said circuit board means and insertable into fluid lines at the inlet and outlet of the in-line filtering means through which the fluid passes for contacting the unfiltered fluid and filtered fluid; and bridge adjustment means operatively connected to said electrode means and to said comparator means to compensate for voltage offsets of said differential bridge means and said differential comparator means, said meter means generating an output indicative of the differential conductivity of the fluid in said inlet and outlet lines of said filtering means;

wherein said differential bridge means detects only the differential conductivity of said unfiltered fluid and said filtered fluid and eliminates the effects of the fluid temperature and the amounts of absolute conductivity of the fluid; and wherein the short actuation of said momentary switch means to detect the difference in fluid conductivity substantially minimizes electrode plating; and indicator means operatively connected to the output means of said differential comparator means for generating an output indicative of the differential conductivity of said fluid.

14. The invention according to claim 13 wherein said bridge adjustment means is comprised of adjustable resistor means.

* * * * *